(12) United States Patent
Greene et al.

(10) Patent No.: US 7,250,251 B2
(45) Date of Patent: Jul. 31, 2007

(54) VIRION-BASED FUSION ASSAY

(75) Inventors: Warner C. Greene, Hillsborough, CA (US); Marielle Cavrois, San Francisco, CA (US); Carlos de Noronha, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 511 days.

(21) Appl. No.: 10/656,803

(22) Filed: Sep. 4, 2003

(65) Prior Publication Data

US 2004/0096823 A1    May 20, 2004

Related U.S. Application Data

(60) Provisional application No. 60/409,401, filed on Sep. 9, 2002.

(51) Int. Cl.
*C12Q 1/70* (2006.01)
(52) U.S. Cl. .................................. 435/5; 424/208.1
(58) Field of Classification Search .................... None
See application file for complete search history.

(56) References Cited

OTHER PUBLICATIONS

Zlokarnik et al., Quantitation of transcription and clonal selection of single living cells with beta-lactamase as reporter. 1998, vol. 279, p. 84-88.*
Chen, Y.D., et al., "On the Use of Self-Quenching Fluorophores in the Study of Membrane Fusion Kinetics—The Effect of Slow Probe Redistribution," Biophys. Chem. 34:283-292 (1989).
Fackler, O. T. et al., "Endocytic Entry of HIV-1," Current Biol. 10:1005-1008 (2000).
Klatzmann, D. R., et al., "The CD4 Molecule and HIV Infection," Immunodef., Rev. 2, 43-66 (1990).
Kowalski, M., et al., "Functional Regions of the Envelope Glycoprotein of Human Immunodeficiency Virus Type 1," Science 237:1351 (1987).
Lifson, J. D., et al., "Induction of CD4-Dependent Cell Fusion by the HTLV-III/LAV Envelope Glycoprotein," Nature 323:725 (1986).
Lowy, R.J., et al., "Observation of Single Influenza Virus-Cell Fusion and Measurement by Fluorescence Video Microscopy," PNAS 87:1850-1854 (1990).
Maddon, P. J., et al., "The T4 Gene Encodes the AIDS Virus Receptor and is Expressed in the Immune System and the Brain," Cell 47, 333-348 (1986).
Maddon, P. J., et al., "The Isolation and Nucleotide Sequence of a cDNA Encoding the T Cell Surface Protein T4: A New Member of the Immunoglobulin Gene Family," Cell 42, 93-104 (1985).
Maddon, P. J., et al., "HIV Infection Does Not Require Endocytosis of its Receptor, CD4," Cell 54:865 (1988).
Marchal, V., et al., "Human Immunodeficiency Virus Type 1 Entry into Macrophages Mediated by Macropinocytosis," J. Virology 75:11166-11177 (2001).
Muthumani et al. "Vpr-GFP Virion Particle Identifies HIV-Infected Targets and Preserves HIV-IV pr Function in Macrophages and T-Cells," DNA Cell Biol. 19:179-188 (2000).
Raviv, Y., et al., "Quantitative Measurement of Fusion of HIV-1 and SIV with Cultured Cells Using Photosensitized Labeling," Virology 293:243-251 (2002).
Wain-Hobson, S., et al., "Nucleotide Sequence of the AIDS Virus, LAV," Cell 40, 9-17 (1985).

* cited by examiner

*Primary Examiner*—Stacy B. Chen
*Assistant Examiner*—Agnieszka Boesen
(74) *Attorney, Agent, or Firm*—Carol L. Francis; Richard A. Schwartz; Bozicevic, Field & Francis, LLP

(57) ABSTRACT

The present invention features methods and compositions relating to a virion-based fusion assay for detection of infection of a target cell by an enveloped retroviral virion such as HIV. The assay uses virions containing a chimeric viral protein comprising a viral accessory polypeptide (such as Vpr) fused to a reporter polypeptide (such as beta-lactamase). Fusion of the virion with a target cell membrane results in intracellular delivery of the chimeric protein to the target cell, which in turn provides for detection of a detectable signal mediated by the reporter polypeptide portion of the chimeric polypeptide. Significant detectable signal is only detected following intracellular delivery of the chimeric viral protein, thus providing for detection of productive viral entry to the exclusion of non-productive, endocytic entry of virions into the cell.

14 Claims, 4 Drawing Sheets

VIRION-BASED FUSION ASSAY

CROSS-REFERENCE TO RELATED APPLICATIONS

This application claims the benefit of U.S. provisional application Ser. No. 60/409,401, filed Sep. 9, 2002, which application is incorporated herein in its entirety.

GOVERNMENT RIGHTS

This invention was made with government support under federal grant no. NIH P01 HD40543 awarded by the National Institutes of Health. The United States Government may have certain rights in this invention.

FIELD OF THE INVENTION

The invention relates to methods and compositions for detection of fusion of an enveloped virus with a target cell.

BACKGROUND OF THE INVENTION

Assays for detection of viral envelope-mediated fusion of an enveloped virion with its host cell has received significant attention since this step represents one of the earliest events in the viral life cycle. Assays for detection of infection of host cells by human immunodeficiency virus (HIV), the etiologic agent of acquired immunodeficiency syndrome (AIDS), is of particular interest. HIV, a member of the lentivirus family of retroviruses, primarily infects helper T lymphocytes and monocytes/macrophages, i.e. cells that express surface CD4, leading to a depletion of CD4+ T lymphocytes.

The initial phase of the HIV replicative cycle involves the high affinity interaction between the HIV exterior envelope glycoprotein gp120 and the cellular receptor CD4 (Klatzmann, D. R., et al., Immunodef., Rev. 2, 43–66 (1990)). CD4 is sufficient to render otherwise infection-resistant cells susceptible to HIV infection (Maddon, P. J., et al., Cell 47, 333–348 (1986)). cDNA clones encoding HIV gp120 and CD4 have been isolated (Maddon, P. J., et al., Cell 42, 93–104 (1985), Wain-Hobson, S., et al., Cell 40, 9–17 (1985)).

Following the binding of HIV-1 gp120 to cell surface CD4, viral and host cell, the HIV gp41, the transmembrane component of the envelope glycoprotein, facilitates fusion of the viral and target cell membranes, resulting in introduction of the viral capsid into the target cell cytoplasm (Maddon, P. J., et al., Cell 54:865 (1988); Kowalski, M., et al., Science 237:1351 (1987)).

Methods for detecting viral fusion events mediated by a viral envelope proteins, such as the HIV-1 envelope glycoprotein, are useful in, for example, identification of agents which alter viral envelope protein-mediated cell fusion.

Conventional assays to examine viral fusion events have principally depended on the use of cell-to-cell fusion assays in which receptor-expressing target cells are cultured with other cells engineered to express the relevant viral envelop gene product. For example, fusion of HIV-1 virions with the host cell plasma membrane has been mimicked by assaying fusion of HIV-1 infected cells expressing gp120/gp41, or by assaying fusion of cells stably expressing recombinant gp120/gp41 with uninfected CD4+ cells (see, e.g., Lifson, J. D., et al., Nature 323:725 (1986)). Although such cell-to-cell fusion studies have yielded valuable information, they do not fully recapitulate all of the variables governing the fusion of actual virions to cellular targets. For example, the density and distribution of the HIV envelope proteins may differ significantly between natural virions and cells engineered to express the HIV-1 env gene products. Furthermore, fusion of HIV in certain cell types such as macrophages (Marchal, V., et al., J. Virology 75:11166–11177 (2001)), or by certain strains of HIV-1 such as SF2 (Fackler, O. T. et al., Curr. Biol. 10:1005–1008 (2000)), may occasionally occur after initial viral entry by macropinocytosis or endocytosis respectively. Thus the assay does not actually detect membrane fusion, but rather only the presence of the virion in the cell within an intracellular compartment, e.g., the viral envelope has not actually fused to provide for delivery of the viral genome to the host cell cytoplasm. Therefore, such processes cannot be recapitulated in cell-to-cell fusion assays.

Only a virion-based fusion assay, applicable to study of viral fusion in primary cells can account for all of these variables that influence the fusion process. Lowy et al. and Chen et al. describe a virion-based fusion assay based on the redistribution of a self-quenching flurophore (Lowy, R. J., et al., PNAS 87:1850–1854 (1990); Chen, Y. D., et al., Biophys. Chem. 34:283–292 (1989)), Raviv et al. describes a virion-based fusion assay based on photosensitized activation of a hydrophobic probe by a fluorescent lipid loaded into the target membrane (Raviv, Y., et al., Virology 293: 243–251 (2002)). These assays are complex, and thus far have not been adapted to study fusion in complex cell populations. Muthumani et al. describes a virion-based fusion assay based on detection of fluorescence from a Vpr-GFP fusion protein present in the virion (Muthumani et al. DNA Cell Biol. 19:179–188 (2000). However this assay does not distinguish between virion entry by endocytosis (a non-productive route of infection) and actual fusion (the productive route of viral entry). Distinguishing between the productive fusion route of entry and the non-productive endocytic route is important, particularly since, in some cells, up to 90% of virions entering the cells do so by the non-productive endocytic route. Thus so far no simple and rapid virion-based fusion assay has been developed.

There still exists a need for a virion-based fusion assay that provides for high sensitivity and specificity for detection of viral fusion events, including detection of a relatively low number of viral fusion events. There is also a need for a virion-based fusion assay that can be applied to detection of viral fusion in biologically relevant cellular targets present in complex cell populations, and which provides for detection using a variety detection methods, such as flow cytometry, fluorescence microscopy, and UV photometry. In addition, the assay should be rapid, reproducible, and quantitative, adaptable to various enveloped virus types and various cell types, and relatively safe (e.g., does not require high titers of enveloped virus).

The present invention addresses these needs.

SUMMARY OF THE INVENTION

The present invention features methods and compositions relating to a virion-based fusion assay for detection of infection of a target cell by an enveloped retroviral virion such as HIV. The assay uses virions containing a chimeric viral protein comprising a viral accessory polypeptide (such as Vpr) fused to a reporter polypeptide (such as beta-lactamase). Fusion of the virion with a target cell membrane results in intracellular delivery of the chimeric protein to the target cell, which in turn provides for detection of a detectable signal mediated by the reporter polypeptide portion of the chimeric polypeptide. Significant detectable signal is only detected following intracellular delivery of the chimeric viral protein, thus providing for detection of productive viral entry to the exclusion of non-productive, endocytic entry of virions into the cell.

In one aspect the invention features a method for detecting fusion of an enveloped retrovirus to a target cell comprising a) contacting a target cell with an enveloped retroviral virion, the virion containing a chimeric viral protein comprising a reporter polypeptide operably joined to a viral accessory protein, wherein the reporter polypeptide provides a detectable signal upon intracellular delivery of the chimeric viral protein into the target cell, which detectable signal is not detectable prior to said intracellular delivery; and b) detecting the presence or absence of the detectable signal. The presence of the detectable signal indicates the virion has fused with the target cell.

In specific embodiments, the enveloped retroviral virion is a human immunodeficiency virus (HIV) virion or a pseudotyped virion having envelope protein that is not endogenous to the retroviral virion. In further specific embodiments, the reporter polypeptide of the chimeric viral protein provides the detectable signal by cleaving a substrate in the target cell, and in some embodiments is beta-lactamase. In still further specific embodiments, the substrate is coumarin cephalosporin fluorescein (CCF2).

In other specific embodiments, the viral accessory protein of the chimeric viral protein is Viral protein R (Vpr), and in further embodiments the reporter polypeptide is beta-lactamase (BlaM). In a specific embodiment of interest, the chimeric viral protein comprises beta-lactamase (BlaM) operably joined to Viral protein R (Vpr), which can be optionally joined through a spacer peptide.

In another aspect, the invention features a method for detecting fusion of an human immunodeficiency virus (HIV) virion to a target cell, the method comprising contacting a target cell with an HIV virion containing a chimeric viral protein, wherein the chimeric viral protein comprises a beta-lactamase(BlaM) polypeptide operably linked to a viral accessory protein, and wherein the cell contains a BlaM substrate so that intracellular introduction of the chimeric viral protein into the target cell results in cleavage of the substrate by BlaM and production of a detectable signal. Detection of the detectable signal indicates that the HIV virion has fused with the cell. In specific embodiments, the viral accessory protein of the chimeric viral protein is Viral protein R (Vpr), and in further embodiments, the chimeric protein comprises BlaM and Vpr, which can be operably linked through a spacer peptide. In further specific embodiments, the HIV virion is a pseudotyped HIV virion, and wherein the envelope protein of the pseudotyped virion is not endogenous to the HIV virion.

In another aspect, the invention features a method for identifying an agent that modulates fusion of a human immunodeficiency virus (HIV) virion to a target cell, the method comprising: a) contacting a target cell with a candidate agent and with an HIV virion containing a chimeric viral protein, wherein the chimeric viral protein comprises a beta-lactamase(BlaM) polypeptide operably linked to a Viral protein R (Vpr) polypeptide, and wherein the cell contains a BlaM substrate so that intracellular introduction of the chimeric viral protein into the target cell results in cleavage of the substrate by BlaM and production of a detectable signal; and b) detecting the presence or absence of the detectable signal. Detection of an increase or decrease in the detectable signal in the presence of the candidate agent compared to detectable signal in the absence of the candidate agent indicates that candidate agent modulates fusion of the HIV virion to the target cell. In specific embodiments, BlaM and Vpr are operably linked through a spacer peptide. In further specific embodiments, the HIV virion is a pseudotyped HIV virion, and wherein the envelope protein of the psuedotyped virion is not endogenous to the HIV virion. In another embodiment, the envelope protein of the pseudotyped virion is an envelope protein of a virus other than HIV.

In another aspect, the invention features a method for identifying a viral envelope protein that facilitates viral fusion to a target cell, the method comprising: a) contacting a target cell with a pseudotyped HIV virion having a non-endogenous viral envelope protein incorporated into the virion envelope, the pseudotyped HIV virion containing a chimeric viral protein comprising a beta-lactamase(BlaM) polypeptide operably linked to a Viral protein R (Vpr) polypeptide, and wherein the cell contains a BlaM substrate so that intracellular introduction of the chimeric viral protein into the target cell results in cleavage of the substrate by BlaM and production of a detectable signal; and b) detecting the presence or absence of the detectable signal. Detection of the detectable signal indicates that the non-endogenous viral envelope protein facilitates viral fusion. In specific embodiments, BlaM and Vpr are operably linked through a spacer peptide. In further embodiments, the non-endogenous viral protein is a naturally-occurring viral protein. In still another embodiment, the method further comprises contacting the target cell with a candidate agent, wherein detection of the detectable signal in the absence of the candidate agent and detection of a decrease in the detectable signal in the presence of the candidate agent indicates the candidate agent inhibits viral fusion facilitated by the non-endogenous viral envelope protein.

In yet another aspect the invention features an isolated chimeric viral protein comprising, operably linked from N-terminus to C-terminus, a beta-lactamase (BlaM) polypeptide, a spacer peptide, and a Viral protein R (Vpr) polypeptide. In specific embodiments, the spacer peptide comprises at least six glycine residues. In related aspects the invention features an isolated polynucleotide sequence encoding the chimeric viral protein, vectors and recombinant cells comprising the chimeric protein-encoding sequence, and enveloped virions containing the chimeric viral protein.

In another aspect the invention features a kit for detecting fusion of an enveloped retroviral virion to a target cell, the kit comprising at least one of: the chimeric viral protein of the invention, an isolated vector comprising a polynucleotide sequence encoding the chimeric viral protein; or an isolated enveloped virion containing the chimeric viral protein. In specific embodiments the kit further comprises a substrate cleavable by BlaM, which substrate is suitable for loading into a target cell.

The present invention provides a rapid and sensitive bioassays for detecting productive viral entry into a target cell, as opposed to other events that may or may not lead to productive infection (e.g., viral attachment to the target cell, or non-productive viral entry via endocytosis). This is accomplished through use of a reporter polypeptide that provides a detectable signal only when present in the target cell cytoplasm.

An advantage of the invention is that, since the assay does not detect viral attachment events or non-productive endocytotic events, the assay avoids the problems of false positive results and overestimate of efficiency of viral infection that can be associated with conventional assays.

A related advantage of the invention is that the background signal associated with attachment and non-productive viral entry events is substantially eliminated, providing a more sensitive and accurate assay which can detect viral entry at the level of single cell viral infection events.

An advantage of the present invention is that it provides a means to detect actual, productive viral-mediated fusion with target cells in a more physiologically relevant environment, using virions and target cells. In contrast to other assays, which employ cells expressing viral envelope proteins in cell-to-cell fusion assays. Therefore the present invention provides an assay that involves all the variables governing the fusion of actual virions to cellular targets by employing an actual virion.

Another advantage of the present invention is that the assays can be adapted for high throughput screening of agents for antiviral activity.

Still another advantage of the invention is that the virions can be pseudotyped with envelope proteins of other viruses, providing an assay for viral fusion events mediated by the non-endogenous envelope protein.

These and other features, and advantages of the invention will become apparent to those persons skilled in the art upon reading the details of the chimeric viral protein and the virion based fusion assay as more fully described below.

DETAILED DESCRIPTION OF THE INVENTION

Overview

The present invention provides a virion-based fusion assay for detection of fusion of an enveloped retroviral virion, such as an HIV virion, to a biologically relevant cell, including primary peripheral blood CD4+ T lymphocytes. This assay involves a chimeric viral protein having a reporter polypeptide operably linked to a viral accessory protein. The reporter polypeptide is one that provides for a detectable signal upon intracellular delivery into a target cell, e.g., by cleaving a substrate present in the target cell. The reporter polypeptide portion is exemplified by beta-lactamase(BlaM); the viral accessory protein is exemplified by-Viral protein R (Vpr).

Fusion of a virion containing the chimeric viral protein with a target cell results in intracellular delivery of the chimeric viral protein into the target cell. The reporter polypeptide portion of the intracellular chimeric viral protein then provides for a detectable signal. The chimeric viral protein provides for a detectable signal upon and substantially only upon intracellular delivery, thus allowing one to distinguish actual, productive entry of the virion by fusion from both non-productive entry (e.g., by endocytosis) and viral attachment to the cell without fusion.

Figure 1:
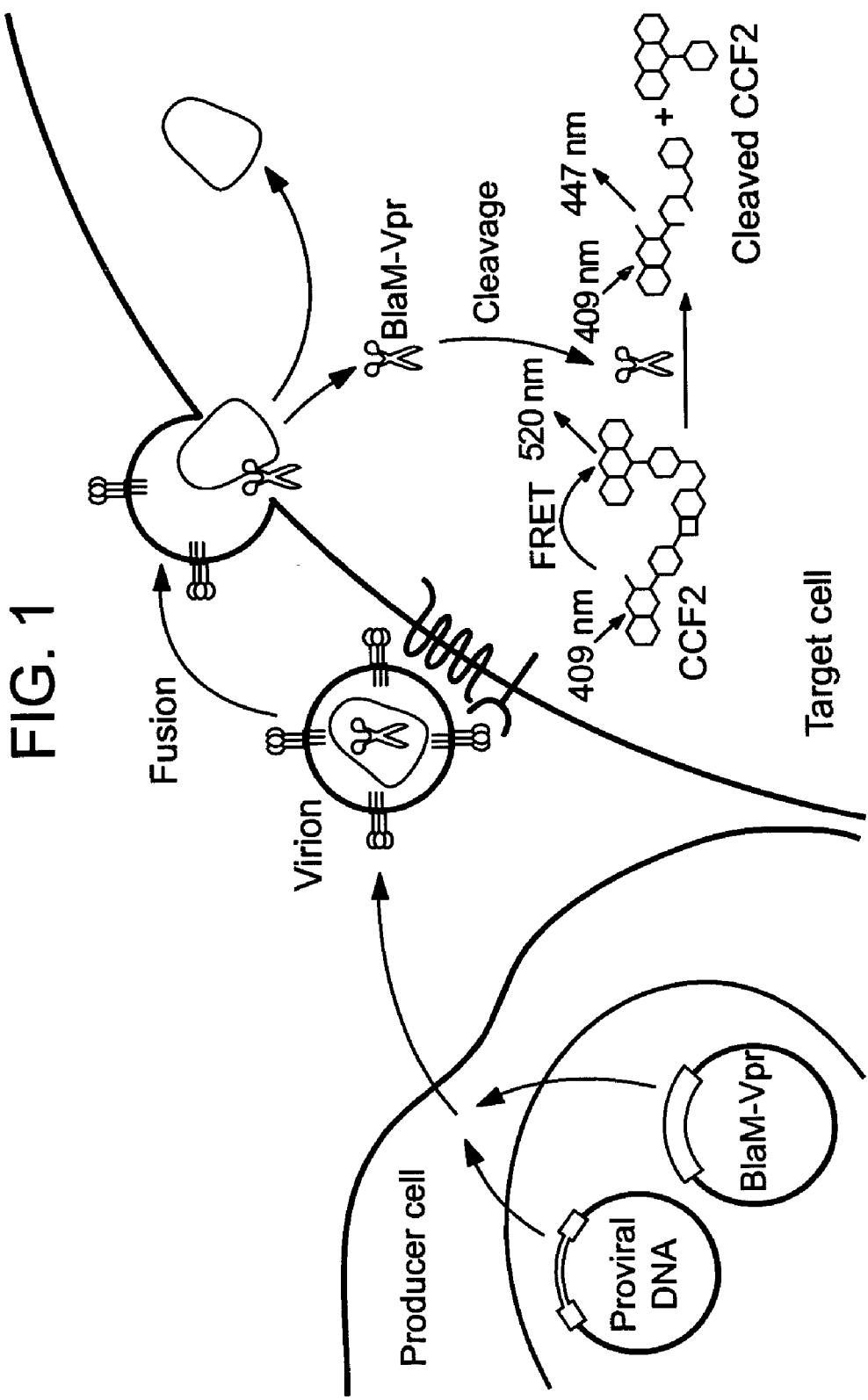
FIG. 1 is a schematic illustrating an embodiment of the virion-based fusion assay of the invention.

One embodiment of the assay of the invention is exemplified in FIG. 1. In this example the chimeric viral protein is a BlaM-Vpr chimeric viral protein and the virus is NL4-3. BlaM-Vpr containing virions are produced using a producer cell having a proviral DNA construct for production of virus particles and a BlaM-Vpr chimeric protein expression construct. The producer cell provides for production of modified virus particles containing the BlaM-Vpr chimeric protein (represented by scissors). The target cell contains a BlaM-Vpr substrate, which in this example is the fluorescent dye CCF2. Fusion of the modified virion with the target cell results in intracellular delivery of BlaM-Vpr to the target cell. The BlaM-Vpr protein cleaves the CCF2 substrate, causing a change in fluorescence emission spectra of the substrate from a green emission (520 nm) to a blue emission (447 nm), thereby providing for detection of viral fusion.

The virus containing BlaM-Vpr is similar to wild type viral particles, but differs in that the virus contains the chimeric protein within the viral particle. In one embodiment, the virion is produced from viral components provided by a proviral DNA present in the host cell. The chimeric viral protein can be encoded on the same or different DNA molecule as the DNA molecule that provides the viral components. Where chimeric protein is present on a different DNA molecule, the DNA molecule can be either episomal or stably integrated into the producer cell genome. The proviral DNA can also provide for expression of a wild-type Vpr, or can be deficient in Vpr.

In one embodiment, the producer cell contains a DNA encoding a heterologous viral envelope protein (i.e., a viral envelope protein that is not normally present in the viral particle encoded by the proviral DNA). Production of the heterologous viral envelope protein in the producer cell provides for the production of pseudotyped viral particles that contain the chimeric viral protein (e.g., BlaM-Vpr). The heterologous envelope protein (e.g., an envelope protein of Ebola virus provided in non-Ebola viral particle) can be present on the same molecule as the proviral DNA, the same molecule as that encoding the chimeric viral protein, or a different molecule, and can be provided as an episomal or stably integrated element in the producer cell. The envelope protein native to the proviral DNA can be deleted or otherwise inactivated so that the heterologous envelope protein is the sole envelope protein of the viral particle.

The virion-based fusion assay of the present invention is simple and rapid to perform. It exhibits a high sensitivity and specificity to fusion events and, importantly, can detect virion fusion occurring in primary cells (e.g., in the case of HIV, CD4+ T lymphocytes present in human peripheral blood, tonsil or spleen). This assay not only offers a powerful tool to dissect virion fusion and to identify new inhibitors of this process, but can also be conveniently adapted to study fusion events mediated by the envelope proteins of other viruses, such as viruses from the filoviridea family, through construction of pseudotyped virions.

The following description provides guidance for making and using the compositions of the invention, and for carrying out the methods of the invention.

Definitions

Unless defined otherwise, all technical and scientific terms used herein have the same meaning as commonly understood by those of ordinary skill in the art to which this invention pertains. Any methods and materials similar or equivalent to those described herein can be used in the practice or testing of the present invention, the described methods and materials being exemplary.

The term "agent" includes any substance, molecule, element, compound, entity, or a combination thereof. It includes, but is not limited to, e.g., proteins (including antibodies), oligopeptides, small organic molecules, polysaccharides, polynucleotides, and the like. It can be a natural product, a synthetic compound, or a chemical compound, or a combination of two or more substances. Unless otherwise specified, the terms "agent," "substance," and "compound" can be used interchangeably.

The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

The term "biological preparation" refers to biological samples taken in vivo and in vitro (either with or without subsequent manipulation), as well as those prepared synthetically. Representative examples of biological preparations include cells, tissues, solutions and bodily fluids, lysates of natural or recombinant cells, and samples derived from such sources.

As used herein, the term "functional derivative" of a native protein or a polypeptide is used to define biologically active amino acid sequence variants that possess the biological activities (either functional or structural) that are substantially similar to those of the reference protein or polypeptide.

The terms "substantially pure" or "isolated," when referring to proteins and polypeptides denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition.

As used herein, "recombinant" has the usual meaning in the art, and refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence" or a "heterologous nucleic acid," as used herein, is one that originates from a source foreign to the particular host cell, or, if from the same source, is modified from its original form. Thus, a heterologous gene in a prokaryotic host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

A "recombinant expression cassette" or simply an "expression cassette" is a nucleic acid construct, generated recombinantly or synthetically, that has control elements that are capable of affecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed and a promoter. Additional factors necessary or helpful in effecting expression can also be used as described herein. For example, transcription termination signals, enhancers, and other nucleic acid sequences that influence gene expression, can also be included in an expression cassette.

As used herein, "contacting" has its normal meaning and refers to combining two or more entities (e.g., two proteins, a polynucleotide and a cell, a cell and a viral particle, etc.). Contacting can occur in vitro (e.g., two or more agents [e.g., a test compound and a cell lysate] are combined in a test tube or other container) or in situ (e.g., two polypeptides can be contacted in a cell by coexpression in the cell, of recombinant polynucleotides encoding the two polypeptides), in a cell lysate"

The term "viral accessory protein" as used herein is meant to refer to a viral protein that is contained in a virion, but which is not an envelope protein, a structural protein, or an enzyme (e.g., reverse transcriptase (RT), integrase (IN), protease (PR), and the like). Viral protein R (Vpr), Rev, Vif and Nef are examples of viral accessory proteins of particular interest, with Vpr being preferred. The accessory proteins are not present in simple viruses and they differentiate the complex virus from the simple virus. For example, Lentiviruses (e.g., HIV family) have Vpr, Rev, Tat, Vif and Nef. The oncomaviruses (e.g., HTLV family) which are also complex retroviruses, encode Tax R, and p12I The term "Vpr" as used herein, refers to "viral protein R", and encompasses any naturally-occurring, retroviral Vpr (particularly HIV Vpr); variants of naturally-occurring Vpr (e.g., variants that include conservative amino acid changes compared to a naturally-occurring Vpr); synthetically or recombinantly produced Vpr. The term "Vpr" further encompasses fragments of Vpr of at least about 20, at least about 50, or at least about 100 amino acids, with the proviso that, when operably linked to a reporter polypeptide in a chimeric viral protein of the invention, the chimeric viral protein can be incorporated into a virion, which virion can mature and be capable of infecting a target cell. The term "Vpr" includes all forms of synthetic Vpr peptides and all fragments thereof chemically synthesized and/or modified by standard methods of peptide synthesis.

The term "producer cell" or "packaging cell" is used herein to refer to a host cell that supports production of viral particles having a chimeric viral protein according to the invention.

The term "target cell" as used in the context of a virion-based fusion assay of the invention refers to a cell, generally a mammalian cell, susceptible to infection or suspected of being susceptible to infection by an enveloped retroviral virion (including pseudotyped retroviral virion) as described herein. Target cells include naturally-occurring host cells (e.g., primary cells from a host susceptible to infection by the virion of interest (e.g., human, primate, feline, an the like), cultured cell lines derived from naturally-occurring host cells, cells expressing a receptor for the virion of interest (e.g., recombinant cells expressing the CD4 receptor for HIV infection), and the like.

By "genetic transformation" is meant a permanent or transient genetic change induced in a cell following incorporation of new DNA (i.e., DNA exogenous to the cell). Genetic change can be accomplished either by incorporation of the new DNA into the genome of a host cell, or by transient or stable maintenance of the new DNA as an episomal element. Where the cell is a mammalian cell, a permanent genetic change is generally achieved by introduction of the DNA into the genome of the cell.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as CD4+ cells, T lymphocytes, macrophages, peripheral blood mononuclear cells (PBMC), and the like. The term "biological sample" encompasses a clinical sample, and also includes cells in culture, cell supernatants, tissue samples, organs, bone marrow, and the like.

As used herein, a "CD4+ cell" is a cell having CD4 affixed to the surface of its cell membrane, wherein the appropriate CD4+ cell is capable of specifically binding to and fusing with an HIV envelope glycoprotein. In one embodiment, the suitable CD4+ cell is a CD4+ HeLa cell. In another embodiment, the suitable CD4+ cell is a PM1 cell. In a further embodiment, the CD4+ cell is a primary human T lymphocyte. In a still further embodiment, the CD4+ cell is a primary human macrophage.

The term "pseudotyped virion" as used herein, refers to a virion having an envelope protein that is not endogenous to the virion. Such pseudotyped virions can further be depleted for or lack the endogenous envelope protein, such that viral attachment is mediated by the non-endogenous viral envelope protein and will mediate fusion after interaction with its specific receptor. As fusion is determined by the envelope protein present at the surface of the virion, the fusion will occur and require the condition dictates by the envelope. For example, if the HIV is pseudotyped with VSV-G (Vesicular Stomatis Viral protein G), the fusion of these pseudotyped virus will only occur after binding of VSVG to a host cell surface receptor and endocytosis of the virus in the acidified endosome.

The term "lentivirus" as used herein, refers to human immunodeficiency virus (HIV, including HIV-1, HIV-2, and the like); simian immunodeficiency virus (SIV); feline immunodeficiency virus (FIV); EIAV, and the like.

ALV (Avian Leukosis Virus) and RSV (Rous Sarcoma Virus) are simple retroviruses of group C retroviruses.

HTLV-1 is a retrovirus of the family of the oncomaviruses, which family also includes STLV-1 (simian form of HTLV), BLV (bovine leukemia virus) and HTLV-2.

The term "filoviridea" as used herein, refers to Marburg virus (MARV); Cote d'Ivoire Ebola virus (CIEBOV); Reston Ebola virus (REBOV); Sudan Ebola virus (SEBOV); and Zaire Ebola virus (ZEBOV).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications (including patents, published applications, and scientific publications, and reference materials) mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an agent that modulates virion fusion" includes a plurality of such agents cells and reference to "the virus" includes reference to one or more viruses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Various biochemical and molecular biology methods referred to herein are well known in the art, and are described in, for example, Sambrook et al., Molecular Cloning: A Laboratory Manual, Cold Spring Harbor Press, N.Y. Second (1989) and Third (2000) Editions, and Current Protocols in Molecular Biology, (Ausubel, F. M. et al., eds.) John Wiley & Sons, Inc., New York (1987–1999).

Chimeric Protein Suitable for Use in Detection of Viral Fusion

In general, chimeric viral proteins suitable for use in the methods of the invention comprise: 1) a reporter polypeptide portion; and 2) a viral protein portion. The chimeric viral protein is incorporated into the virion particle such that, upon fusion of the virion with a target cell, the chimeric viral protein is delivered intracellularly into the target cell. Following intracellular delivery, the reporter polypeptide provides for a detectable signal, e.g., by cleaving a substrate present in the target cell.

Use of a chimeric viral protein allows for delivery of the reporter polypeptide partner in functional form, without the need for transcription or translation (as in a scheme using a polynucleotide encoding a reporter polypeptide). As such, the reporter polypeptide portion of the chimeric viral protein enables rapid production of a detectable signal, facilitating sensitive detection of fusion between the virion and target cell. Furthermore, because the reporter polypeptide detectable signal substantially only occurs after the fusion event has occurred (and not, for example, at the point of virion attachment to the target cell membrane), the assay is specific for viral fusion events.

The components of the chimeric viral protein are described in more detail below.

Viral Polypeptide Portion of the Chimeric Viral Protein

Viral polypeptides useful in the chimeric viral protein of the invention are generally any viral polypeptide that is delivered intracellularly into the target cell following virion fusion. Of particular interest are viral polypeptides that: 1) can be provided as a fusion protein without undesirable adverse effect on the ability of the virion to form or mature; 2) are incorporated into the virion in a sufficient amount (so that the reporter polypeptide associated in the chimeric viral protein can provide for a detectable signal following intracellular delivery); and, 3) where the incorporation of the viral polypeptide into the chimeric viral protein impairs a function of the viral polypeptide necessary or important for virion production in a producer cell, the function of the viral polypeptide can be complemented by co-expression of an unmodified viral polypeptide. In some embodiments, complementation is not necessary, so long as the chimeric viral protein does not impair fusion or production of the virus in the producer cell. For example, Vpr-deficient HIV virus is not impaired in fusion, but are defective for replication in a host cell, e.g., macrophage. Since the present assay is not dependent on viral replication in the host cell, the defect in Vpr need not be complemented.

In view of these requirements, viral accessory proteins are of particular interest for use in the chimeric viral proteins of the invention. Exemplary retroviral viral accessory proteins include, but are not necessarily limited to, Viral protein R (Vpr), Vif, Vpu, Nef, and the like. Retroviral Vpr, particularly an HIV Vpr, is of particular interest. Viral protein R (Vpr), is also referred to as "lentiviral R protein" since it is common to all known primate lentiviruses, including HIV-1, HIV-2 and SIV. The polynucleotide and amino acid sequences of Vpr of various retroviruses are available in the art (see, e.g., GenBank Accession Nos. AF457101, NC_001802, AB052995 (complete genomes of various HIV-1 isolates); NC_001722, L36874, AF208027, (complete genome of various HIV-2 isolates); Y16029, Y16028, Y16028, Y16028, K02012 (HIV-1 genes, including vif, vpr, tat, and vpu); U81843, U81842 (HIV-2 vpr); AF468659, AF468658 (SIV complete genome); Y16028, U20965, (SIV Vpr).

Vpr of HIV-1 is a 96-amino acid, 14 kD protein that performs two distinct functions during HIV replication. Vpr is incorporated into the HIV virion and helps to target the viral preintegration complex (PIC) to the nucleus in nondividing cells via its nuclear localization signal. An interaction between Vpr and the p6 portion of the Gag protein is believed to be responsible for the packaging of Vpr into the virion. Vpr is also responsible for arresting HIV infected cells in the G2 phase of the cell cycle, which results in increased virus production. The mechanism of G2 cell cycle arrest is unknown, but Vpr expression has been correlated with a decrease in p34cdc2/cyclo B complex activity. Due to the binding of Vpr to the p6 component of the Gag polyepetide, a Vpr chimeric viral protein is incorporated into virion at significant levels.

Reporter Polypeptide Portion

The reporter polypeptide portion of the chimeric viral protein elicits a signal following intracellular delivery of the chimeric protein into the target cell. In general, reporter polypeptides that are suitable for use in the methods described in the present invention include: 1) a polypeptide that acts upon a substrate, thereby producing a detectable signal (e.g., a fluorescent signal, including a shift in the emission wavelength of a substrate following action of the reporter polypeptide), and thus the signal is provided by the combined action of a reporter polypeptide-substrate pair; or 2) a reporter polypeptide that emits a signal that is detectable upon intracellular delivery, but substantially not prior to intracellular delivery (e.g., the reporter polypeptide emits a fluorescent signal that is not detectable or detectable at very low levels prior to intracellular delivery, and provides a detectable signal that is significantly greater than the signal prior to intracellular delivery, e.g., a shift in emission wavelength upon exposure to the intracellular milieu.

Reporter Polypeptide—Substrate Pairs

In embodiments of particular interest, the reporter polypeptide elicits a detectable signal by acting upon a substrate. In one embodiment of the present invention, the reporter polypeptide is an enzyme that cleaves a substrate present in the target cell, where cleavage of the substrate results in production of a detectable signal. An example of such reporter polypeptides of particular interest includes, but is not necessarily limited to, beta-lactamase. Other enzymes for which suitable substrates may be available includes beta-galactosidase.

The substrate of the enzyme-substrate pair must generally be one that 1) can be introduced into intact cells (e.g., by diffusion of the substrate due to permeability of target cell membrane to the substrate (i.e., to allow for "loading" of the target cell with the substrate) or expression of the substrate in the target cell from a recombinant polynucleotide encoding the substrate), 2) remains cleavable by the reporter enzyme when present in the intracellular milieu, and; 3) is retained in the cytoplasm (e.g., is not present at detectable or significantly detectable levels in endosomes). Retentinof the substrate in the cytoplasm can be accomplished by an appropriate modification of the substrate, e.g., the action of a cytoplasmic esterase for esterification and retention of the substrate, as with the substrate CCF2. Where the infection is performed after loading of the target cell, the substrate should not substantially affect the integrity of the target cell or susceptibility of the target cell to viral infection.

The substrate is loaded (introduced) into the target cell prior to, during, or following contact with a modified virion of the invention.

In some embodiments, the substrate is endogenous to the target cell, and the cleaved substrate is detected using a third reagent. For example, reporter polypeptide can be a kinase that phosphorylates a specific residue(s) of a specific endogenous protein following or upon intracellular, cytoplasmic delivery. Phosphorylation of the endogenous protein may then be detected by, for example, immunostaining using an antibody specific for the phosphorylated residue of the endogenous substrate.

A preferred, non-limiting reporter polypeptide: substrate pair is beta-lactamase and CCF2 (used interchangeably herein with CCF2/AM, the modified form to which target cell membranes are permeable). Other reporter polypeptide: substrate pairs may be provided by, for example, appropriate modification of the substrate to provide for the cytoplasmic retention feature described above.

In one embodiment of particular interest, the reporter polypeptide portion of the chimeric viral protein is beta-lactamase and the substrate is CCF2. Target cells are loaded with CCF2/AM, a membrane permeable form of the CCF2 dye. CCF2/AM undergoes de-esterification of the dye by non-specific cytoplasmic esterases in the cell cytoplasm, producing non-membrane permeable CCF2, which is largely trapped within cells. Cytoplasmic retention of the substrate can be further improved by control of assay temperature and/or addition of probenecid to inhibit the action of anion transporters that export CCF2 from the cell.

In this embodiment, target cells are loaded with CCF2/AM ester prior to, during, or following contact with a modified virion. At an excitation wavelength of about 409 nm, CCF2 dye displays a fluorescence emission at 520 nm (green) reflecting effective fluorescence resonance energy transfer (FRET) from a 7-hydroxy coumarin ring to fluorescein physically joined through a cephalosporin bridge containing a β-lactam ring. The beta-lactamase-containing chimeric viral protein cleaves the beta-lactam ring of CCF2 to disrupt this FRET, and causing the fluorescent emission of the compound to shift to a fluorescence emission wavelength of 447 nm (blue). Thus, uninfected target cells (i.e., target cells that have not fused with a modified virion) appear green, which infected target cells appear blue.

Spacer Peptide

In some embodiments, the chimeric viral protein comprises a spacer peptide operably linked between the reporter polypeptide and the viral accessory polypeptide portions. "Spacer peptide" as used herein refers to a peptide of at least 4, 6, 8, 10, 12, 15, or more amino acids. The spacer peptide links the two components, providing for sufficient distance between the two polypeptide moieties so that each retains their biological activity. In short, the envelope protein domain of the chimeric viral protein must be able to retain its ability to interact with the other viral proteins to provide for incorporation of the chimeric protein into virions. In addition the reporter polypeptide must retain its ability to produce a detectable signal upon its intracellular introduction into the target cell (e.g., activity in cleaving a substrate). The spacer peptide can have any suitable amino acid sequence, with amino acids having aliphatic side groups being of particular interest, e.g., glycine, alanine, valine, leucine, and/or isoleucine, with glycine being preferred. Where fragments of the viral accessory polypeptide and/or the reporter polypeptide are used, a longer spacer peptide (e.g., corresponding to the number of amino acids deleted in the chimeric protein component relative to the full-length component) may be used, e.g., to ensure a sufficient distance between the relevant regions of the polypeptides required for activity.

In some embodiments it may be preferred that the reporter polypeptide be positioned N-terminal to the viral polypeptide in the chimeric viral protein, such that the chimeric protein has the formula:

R-Xn-V where R is the reporter polypeptide; X is a spacer peptide having n amino acid residues, where n is at least 4, 6, 8, 10, 12, 15, or more amino acids; and V is a viral accessory polypeptide. In other embodiments, the spacer peptide may be omitted, and thus the value n for X may be zero.

In one embodiment of particular interest, the chimeric viral protein comprises beta-lactamase, Vpr, and a spacer peptide having at least six glycine residues, where the spacer peptide is joined to the C-terminus of beta-lactamase and to the N-terminus of Vpr.

Modified Virions

The virions of the invention are generally an enveloped retrovirus containing a chimeric viral protein within the virion so that fusion of the virion with a target cell results in intracellular delivery of the chimeric viral protein to the target cell. Virions of particular interest include, but are not limited to primate lentiviruses (e.g., human immunodeficiency virus (HIV, including HIV-1, HIV-2, and the like); simian immunodeficiency virus (SIV)). Other retroviruses of interest for production of modified virions having a chimeric viral protein include, but are not necessarily limited to viruses of the oncornaviruses (HTLV-1, HTLV-2, STLV-1, BLV, and the like).

In one embodiment of particular interest, the virion is an HIV, particularly HIV-1 or HIV-2, more particularly HIV-1.

The modified virions can be modified for other viral components, e.g., having a modified envelope protein, modified reverse transcriptase, and the like. The modified virions can be capable of replication or be replication deficient. The modified virions can be useful in examining the effects of genetic modification of the viral genome upon infection of a target cell.

Pseudotyped Virions

In one embodiment of the present invention, the modified virion containing a chimeric viral protein of the invention is a pseudotyped virion. A "pseudotyped virion" as used herein refers to a virion having an envelope protein that is provided in trans to the other viral proteins for production of the viral particle, usually a non-endogenous viral envelope protein (e.g., is other than the naturally-occurring envelope protein of the virion). In some embodiments, the modified virion may be depleted in or lack the corresponding endogenous viral protein. For example a pseudotyped virus having a non-endogenous envelope protein may be deficient or lacking in the native envelope protein, so that attachment of the virion to a target cell is mediated by the non-endogenous envelope protein. The non-endogenous viral protein can be a naturally-occurring protein of a different virus (e.g., a virus of a different strain, species, genus, family, and the like), or may be a modified envelope protein (e.g., produced through recombinant techniques so as to be modified relative to its naturally-occurring counterpart by, e.g., deletion, addition, substitution, and/or insertion of one or more amino acid residues).

In some embodiments, the envelope protein for production of pseudotyped viral particles is endogenous to the viral particle, but is provided in trans to the viral genome (e.g., the proviral DNA). This embodiment is of particular interest where it is desirable to produced replication deficient viral particles lacking nucleic acid encoding the viral protein provided in trans. For example, a pseudotyped HIV can be produced where the HIV genome lacks the endogenous envelope protein, which is provided in trans. Such particle psuedotyped HIV particles can undergo a single round of infection, but will not produce infectious particles in the target cell.

Of particular interest are virions pseudotyped for an envelope protein of another virus, e.g. the viral envelope proteins of the marburg virus or other members of the filoviridea family of viruses. Examples of viruses whose envelope proteins may be used in production of pseudotyped viruses for use in the assays of the invention include, but are not limited to, *Haemophilus influenzae* (Flu), Herpes Simplex virus (HSV), Hepatitis B virus (HBV), Hepatitis C virus (HCV), Human T-cell Lymphotrophic virus type I (HTLV-I), Sindbis virus (SIN), filoviruses, including Ebola Marburg, Ebola Zaire, Ebola Sudan, Ebola Ivory Coast, West Nile Fever virus, and the like. As described in more detail below, methods of producing a pseudotyped virus are known in the art and can be readily adapted in the production of the modified virions of the invention having a chimeric viral protein.

Use of pseudotyped virions in the assay of the invention provides for, for example, methods for identification of viral proteins that facilitate infection of a target cell (e.g., identification of viral envelope proteins), identification of agents (including cellular proteins that may act as receptors or co-receptors, and the like) that modulate (e.g., increase or decrease) viral fusion mediated by the viral envelope protein, identification of target cells susceptible to infection by the virus form which the envelope protein present in the pseudotyped virion is derived, and the like.

Producer Cells and Production of Modified Virions

The invention also features cells for production of modified virions, referred to herein as "producer cells". In general, producer cells are mammalian cells that support production of enveloped retroviruses for production of a modified virion according to the invention. Preferably, the producer cell is one that can be readily propagated in culture and is readily manipulated using recombinant techniques. Exemplary producer cells, include, but are not necessarily limited to, mammalian cell lines (particularly human cell lines), such as 293T cells, HeLa cells, and the like.

In general, producer cells are generated by introduction of one or more constructs for expression of proviral DNA and of a chimeric viral protein of the invention. The polynucleotide e.g., plasmid, encoding the proviral DNA and the polynucleotide (e.g., plasmid) encoding the chimeric viral protein may be on the same or different expression constructs. The constructs can be introduced into the host cell by any one of the standard means practiced by one with skill in the art to produce a producer cell of the invention. Introduction of the proviral DNA and the chimeric protein-encoding polynucleotide results in production of viral particles containing the chimeric viral protein. The modified viral particles are released from the producer cells, and the modified virions can be harvested from the cell culture supernatant.

In one embodiment, the proviral DNA encodes the native viral protein that is present in the chimeric viral protein. For example, the proviral DNA encodes a native Vpr and the chimeric viral protein contains Vpr as the viral polypeptide portion. Thus, modified virions produced from these producer cells will contain native Vpr as well as the chimeric viral protein. This embodiment is particularly suited for use with a chimeric viral protein having a reporter polypeptide portion that requires only a few molecules to produce a detectable signal in the target cell following fusion. For example, fewer than 100 molecules of BlaM can be readily detected in a target cell loaded with substrate. Chimeric viral protein comprising BlaM fused to Vpr take advantage of the fact that retroviral virions (e.g., HIV) can incorporate several hundred Vpr molecules through assembly with the p6 component of the Gag polyprotein. Thus, the assay sensitivity is not significantly affected by incorporation of native viral proteins and chimeric viral proteins into the virion.

In other embodiments, the proviral DNA is deficient for production of the viral protein that is present in the chimeric viral protein. For example, where the chimeric viral protein comprises Vpr, the proviral DNA is modified to decrease or eliminate Vpr production. In this embodiment, Vpr of the virion is replaced by the chimeric Vpr protein.

An expression construct encoding the chimeric viral protein can be stably integrated into the producer cell line. In addition or alternatively, the proviral DNA or portions thereof, can be stably integrated into the producer cell line or transmitted to the producer cells by infection with various HIV strain including primary isolates. Expression of one or more of the chimeric viral protein or native viral proteins (e.g., gag, pol, and the like) can be made inducible by operably linking the relevant coding region to an inducible promoter, e.g. tetracycline inducible expression system or using a LTR as a promoter which will be inducible upon expression of Tat (Invitrogen).

In one embodiment, an expression construct encoding a chimeric viral protein is stably integrated in a cell line that is susceptible to infection by a particular enveloped retrovirus virus, e.g. HIV-1, to provide a recombinant producer cell that constitutively or inducibly expresses the chimeric viral protein. This recombinant producer cell can then be infected with an enveloped retrovirus of interest for production of modified virions having the chimeric viral protein. This embodiment is particularly useful in the production of modified viral particles from a retrovirus isolated from a patient sample for diagnostic testing and study. Viral particles isolated from a patient are passaged through the cell line. Expression of the chimeric viral protein during production of new viral particles by the recombinant producer cells results in incorporation of molecules of the chimeric viral protein into the envelopes of the newly produced virions. These modified viral particles produced from a clinical isolate can then be used in the virion based fusion assay of the invention in order to provide for identification of the retrovirus in the clinical sample, to examine viral fusion for the particular strain, to identify agents that inhibit viral fusion by the clinical isolate, and the like.

Production of Pseudotyped Virions Having a Chimeric Viral Polypeptide

In one embodiment of the present invention, the modified virion containing a chimeric viral protein of the invention is a pseudotyped virion, as discussed above. Methods for producing a pseudotyped virus are known in the art and can be readily adapted in the production of the modified virions of the invention having a chimeric viral protein. See, e.g., U.S. Pat. Nos. 6,218,181; 6,117,681; 5,750,396; 5,739,018; and 5,817,491. Exemplary production methods involve infection of a producer cell for production of the modified virions of the invention with a virus having an envelope protein of interest for incorporation into the modified virion. This method does not require isolation or cloning of the viral proteins of interest, as infection of the producer cell with the virus of interest will provide for expression of the envelope protein in the cell, and its incorporation into the modified virions having the chimeric viral protein.

Where the relevant polynucleotide encoding the viral protein of interest has been cloned, the polynucleotide can be expressed in the producer cell to provide for production of, for example, the protein of interest for incorporation into the modified virions of the invention.

In one example, production of pseudotyped viral particles for use in a fusion assay of the invention can be carried out in the following manner. A first polynucleotide is provided, which contains proviral DNA for a virus of interest (e.g., HIV-1) that is to provide the basis for the modified virion, however the proviral DNA is deficient in the env (envelope) gene. A second polynucleotide is provided that encodes an envelope protein of a different virus, e.g., Ebola virus (see, e.g., GenBank accession no. U31033). A third polynucleotide is provided which encodes the chimeric viral protein of the invention, e.g., BlaM-Vpr. The first, second, and third polynucleotides may provided in the same or different vectors for expression. For example, each of the first, second, and third polynucleotides may be provided on separate expression vectors, the first and third polynucleotide (the proviral DNA and the chimeric viral protein) may be provided on the same expression vectors, and so on.

The three polynucleotides are then introduced into a producer cell. Once transfected, the HIV-1 proviral DNA provides for production of viral particles. During assembly, the envelope protein of Ebola virus is incorporated into the HIV-1 viral envelope, and the BlaM-Vpr is contained within the virion. The resulting viral particles are HIV-1 virions pseudotyped with the viral envelope protein of Ebola virus. The Ebola pseudotyped virions are then contacted with a candidate target cell. Viral fusion indicates that the target cell has a cell surface receptor for the Ebola envelope protein.

Target Cells

Numerous cell types can be used as target cells in the virion based fusion assay of the invention. The type of cell that is chosen for use is dependent on the type of virion upon which the modified virion is based (i.e., the virus that provides the proviral DNA in the production of the modified virion).

In one embodiment of the invention the modified virion particle is based upon an enveloped virus of the Lentivirus family. More specifically, the modified virion particle is based upon an HIV virus, e.g., HIV-1, HIV-2. In this embodiment, the target cell is one that expresses, or is modified to express, on its cell surface the HIV receptor and, if necessary, other host cell proteins necessary to mediated HIV fusion to the target cell (e.g. CD4 receptor and any necessary co-receptor that facilitates viral fusion (e.g., CXCR4, CCR5, and the like)).

The target cells can be isolated primary cells, primary cells in a mixed culture, cell lines, recombinant cells expressing the necessary components for viral attachment and fusion, and the like. Where the modified virion is based upon HIV, exemplary target cells include, but are not necessarily limited to, macrophages, dendritic cells, primary cells such as peripheral blood mononuclear cells (PBMC), human lymphoid aggregate cultures (HLAC) (e.g., from tonsil or spleen), CD4-positive T-cells (e.g., primary T cells, Jurkat cells, CEM SupT1 cells), CD4-positive cell lines (e.g., CD4-positive HeLa cells, HLK cells), and the like.

Assays

The virion based fusion assay of the present invention is generally conducted by contacting a modified virion having a chimeric viral protein with a target cell, which cell is susceptible to infection (or suspected of being susceptible to infection) by the enveloped retrovirus upon which the modified virion is based. For example, where the modified virion is modified HIV virion having chimeric viral protein incorporated within the virion, the target cell is on the is susceptible to infection by HIV, or suspected of being susceptible to infection by HIV.

The modified virion is contacted with the target cell under conditions (e.g., time, temperature, etc.) suitable for infection, minimally for viral attachment and viral envelope-target cell membrane fusion that provides for intracellular delivery of the chimeric viral polypeptide to the target cell. Where the reporter polypeptide of the chimeric viral protein provides a detectable signal by cleaving a substrate, the target cell is loaded with the substrate prior to infection, concurrently with infection, or after infection. Conditions suitable for viral fusion to a target cell are well known to those skilled in the art. The relative number of target cells and modified virions (e.g., the ratio of virions to target cells) used can be optimized to provide for rapid detection of any viral fusion event, or for detection of single fusion events (e.g., detection of fusion of a single modified virion with a target cell).

While a washing step can be used to remove excess modified virions from the target cells, such may not be necessary since a detectable signal indicative of viral fusion is only substantially detectable when the fusion event has actually occurred. Thus, excess virions in the assay that do not result in fusion events are not associated with any significant background signal that may frustrate detection of actual fusion events.

After a time sufficient to allow for infection of the target cell and any membrane fusion events, the detectable signal is detected using a suitable method. For example, where the detectable signal is a fluorescent signal that results from cleavage of a substrate by the reporter polypeptide portion of the chimeric protein, the detectable signal can be assayed using fluorescence microscopy, ultraviolet photometry, flow cytometry by means of a fluorescence-activated cell sorter, and the like.

Assays of the present invention are generally conducted in vitro, however in some embodiments the assay may be conducted in vivo. For example, a non-human animal susceptible to infection by the virus upon which the modified virion is based (e.g., HIV) can be inoculated with an amount of the modified virus in an amount sufficient to provide for infection of target cells of the animal. The non-human animal can be an animal that is naturally susceptible to infection, or that is modified to contain a target cell susceptible to infection (e.g., transgenic or chimeric non-human animals). Exemplary non-human animals include, but are not necessarily limited to non-human primates, rodents (e.g., mice, rats, and the like), ungulates (e.g., cows, goats, pigs, etc.), lagomorphs (e.g., rabbits, guinea pigs, etc.), avian species (e.g., chickens, etc.), scid-Hu chimeric non-human animals (e.g., cidHu mice), and the like. Following inoculation, the target cells may be isolated from the animal model and assayed for infection by any number of methods known in the art (e.g., by flow cytometry using a Fluorescence-Activated Cell Sorter (FACS), and the like).

The assays of the invention can be adapted to provide for a high throughput assay. For example, target cells may be cultured in multi-welled plates, whereby many different assay can be conducted in parallel.

Various embodiments of the assays of the invention will now be described in more detail.

Screening Methods to Identify Modulators of Viral Fusion (e.g., Antiviral Agents)

In one embodiment, the invention features application of the virion-based fusion assay to identify agents that modulate virion and target cell fusion.

Candidate Agents in Drug Screening Methods

Candidate agents encompass numerous chemical classes, though in this embodiment of the invention are typically organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts (including extracts from human tissue to identify endogenous factors affecting virion and target cell fusion) are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Drug Screening Assays

The virion-based fusion assay of the invention a describe above is conducted in the presence and absence of one or more various candidate agents. Agents that inhibit viral fusion with a target cell are associated with a decrease in detectable signal relative to assays conducted in the absence of the agent. Conversely, agents that promote viral fusion with a target cell are associated with an increase in detectable signal relative to assays conducted in the absence of the agent. Agents that inhibit viral fusion (e.g., by inhibiting viral attachment or viral fusion) are of particular interest as antiviral agents. Agents that exhibit low toxicity for human cells are also of particular interest. Also of interest are antibodies that inhibit viral fusion. Such antibodies, and/or the antigens that elicited such antibodies, can then be used as the basis for a vaccine.

High-throughput assays can be conducted in vitro to identify viral fusion modulating agents can be conducted in parallel, e.g., with different agents and/or different concentrations or amounts of agent. High-throughput assays provide the added advantage of examining the activity (e.g., potency, toxicity) of various agents in relation to each other. For example, a high-throughput assay can facilitate identification of agents having differing potency in modulating a fusion event.

Such assays can be conducted using the various modified virus particles described herein. For example, the assay can be conducted with a modified virion having an envelope protein endogenous to the virion from which the modified virion is produced (e.g., a modified HIV virion having the endogenous HIV envelope protein). Alternatively, the assay can be conducted with a pseudotyped modified virion (e.g., a pseudotyped HIV modified virion having an Ebola virus envelope protein). Thus the assay of the invention can be applied to, for example, identify viral fusion inhibitors for untreatable pathogens (e.g., Ebola or Marburg virus), as well as to identify new viral fusion inhibitors having improved characteristics (e.g., efficacy, toxicity, etc.).

Methods to Identify Viral Proteins that Mediate Viral Fusion

In another aspect of the present invention, the fusion assay is used to identify viral or host cell proteins that mediate viral and target cell fusion. For example, the modified virion may contain the chimeric viral protein and also be modified in one or more non-endogenous viral proteins to examine the role of the protein in viral attachment and/or fusion. Non-endogenous viral proteins can include, for example, an endogenous viral protein that is modified by deletion, addition, substitution, or insertion of one or more amino acids. Alternatively, the non-endogenous viral protein may be a viral protein of a virus of a different strain, species, genus, or family (e.g., an HIV virion can be modified to have incorporated an envelope protein of a non-HIV virus). The virion can be deficient in the corresponding endogenous viral protein (e.g., the HIV envelope protein can be deleted from the proviral DNA and the virion pseudotyped with Ebola virus envelope protein or a modified HIV envelope protein). The virion-based fusion assay is conducted with such modified viral particles, and the efficiency of viral fusion compared to that of modified virion having the endogenous viral protein.

Methods to Identify Target Cell Proteins that Mediate Viral Fusion (e.g. Viral Receptors and Co-Receptors)

The modified virions, pseudotyped modified virions, and assay of the invention can be adapted to identify target cells susceptible to infection, and to identify target cell receptors and co-receptors that mediate viral fusion. In this embodiment the target cells can be any cell, usually a mammalian cell, for which susceptibility to viral infection is to be assessed, including primary cell, cell lines, and cells genetically modified to express a candidate viral receptor and/or co-receptor. Target cells of known susceptibility to infection by the modified virion serve as a control.

For example, a mixed population of candidate target cells or isolated candidate target cells in parallel assays can be contacted with a modified virion having a BlaM-Vpr chimeric protein. The candidate target cells are loaded with a BlaM substrate, such as CCF2. Candidate target cells susceptible to viral fusion are readily identified by the detectable signal produced by intracellular BlaM-Vpr. These viral fusion-positive cells can be further characterized using reagents to detect cell surface markers (e.g., antibodies to various cell differentiation antigens), and analysis using, for example, FACS. Where the candidate target cell is present in a mixed cell population, viral fusion-positive cells can be separated by FACS.

In one embodiment, a cDNA library representing various candidate viral receptor or co-receptor-encoding sequence is introduced into host cells to provide a library of recombinant target cells expressing different candidate viral receptors or co-receptors. The target cell library is then assayed according to the invention to identify those recombinant target cells that are susceptible to infection, with a target cell(s) of known viral infection susceptibly serving as controls. The target cell library can be assayed using pools of recombinant target cells or isolated recombinant target cells in separate assays. Recombinant target cells susceptible to infection are identified by detection of the detectable signal generated by the chimeric viral protein. Where the assay is performed with a pool of recombinant target cells, the viral fusion positive cells can be isolated using FACS. The cDNA and its encoded protein of the infected recombinant target cell can be further characterized for its role in mediating viral fusion.

Diagnostic Methods and Methods of Screening Clinical Isolates to Facilitate Rational Therapy In yet another embodiment, the assay of the invention can be used as a diagnostic tool to determine the binding and fusion functions of virions isolated from a particular patient. In this embodiment, a modified viral particle is produced from a retrovirus isolated from a patient sample. Viral particles isolated from a patient are passaged through a producer cell line. The producer cell contains a polynucleotide encoding a chimeric viral protein (e.g., BlaM-Vpr), which chimeric protein can be constitutively or inducibly expressed by the producer cell. Expression of the chimeric viral protein during production of new viral particles by the infected, recombinant producer cells results in incorporation of molecules of the chimeric viral protein into the envelopes of the newly produced virions. These modified viral particles produced from a clinical isolate can then be used in the virion based fusion assay of the invention in order to provide for further characterization of the retrovirus in the clinical sample, to examine viral fusion for the particular strain, to identify agents that inhibit viral fusion by the clinical isolate, and the like. In this manner, an appropriate therapy can be selected for the patient according to the antiviral agent effective in inhibiting fusion of the modified virion to the target cell.

In a related embodiment, the assay is adapted to facilitate diagnosis of a retroviral infection in a subject. A clinical sample suspected of containing a retrovirus is obtained from the subject, and is contacted with recombinant producer cells that express a chimeric viral protein, exemplified here by BlaM-Vpr. After a time sufficient for infection and production of modified virions by any infected producer cells, a sample of the supernatant is collected and the presence of modified virions is determined by contacting the sample with a target cells loaded with the CCF2 substrate. Detection of viral fusion with the target cells indicates that the sample of producer supernatant contained modified virions, which in turns indicates that the producer cells were infected with a retrovirus that was present in the clinical sample.

Kits

The present invention further provides kits for use in the assay of the invention. The kit can comprise, in separate compartments or containers, one or more of the following: 1) a construct encoding a chimeric viral protein (e.g., BlaM-Vpr); 2) a suitable recombinant producer cell that is or can be modified to constitutively or inducibly express a chimeric viral protein (e.g., BlaM-Vpr); 3) a substrate for the reporter polypeptide of the chimeric viral protein (e.g., CCF2/AM, where the chimeric protein comprises BlaM); and 4) a target cell of known susceptibility to viral infection.

The components of the kits may be modified commensurate to the disclosure provided above. For example, the producer cells may be engineered to be express either of or both of the chimeric viral protein and a proviral DNA of a retrovirus, making the kit readily useful in antiviral drug screening assays.

The kits of the present invention may further comprise additional buffers. Furthermore, the cells may be either freeze died or suspended in a liquid or gel carrier. The kits can include suitable amounts of cells, which amounts are those that would, for example, permit one skilled in the art to determine, without undue experimentation, whether an agent is capable of modulating the fusion of a target cell and an enveloped virion. Such amounts may be readily determined according to methods well known to those skilled in the art.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials are used in the below.

Construction of the β-lactamase(BlaM)-Vpr Chimeric Viral Protein

The β-lactamase coding region present in the GeneBLAzerTM β-lactamase vector (Aurora Biosciences, San Diego, Calif.) was directionally inserted into pcDNA3.1 as a HindIII-EcoRI fragment to form pcDNA3.1-BlaM.

For construction of the BlaM-Vpr chimeric viral protein, first a PCR fragment containing the BlaM gene was generated from the pcDNA3.1-BlaM vector. The BlaM fragment was amplified using the sense primer 5'-cccAAGCTTccaatgcttaatcagtgaggcacc-3' and the anti-sense primer 5'-cccAAGCTTgccaccaccaccacccaatgcttaatcagtgaggcacc-3'. The PCR fragment was subsequently digested by using HindIII and cloned into the HindIII site of pCMV4-HA-Vpr (de Noronha, C. M. et al., Science 294:1105–1108 (2001)). The β-lactamase gene was linked to the N-terminus of Vpr, separated by a six-residue glycine spacer. The plasmid pCMV-BlaM-Vpr was generated from the cloning steps, and was subsequently verified by DNA sequencing.

Production of β-lactamase-Vpr Containing Viral Particles

HIV-1 virions containing the BlaM-Vpr fusion protein were produced by cotransfection of 293T cells plated in 175 cm2 flasks with pNL4-3 proviral DNA (60 µg), pCMV- BlaM-Vpr (20 μg) and pAdVAntageTM vectors (10 μg) (Invitrogen). After 48 hours of culture at 37° C., the virus-containing supernatant was centrifuged at low speed to remove cellular debris and then ultra-centrifuged at 72,000×g for 90 min at 4° C. to sediment viral particles. The virion enriched pellet was re-suspended in DMEM and aliquoted for storage at −80° C. All transfections were performed using calcium phosphate for precipitation of DNA. Viral stocks were normalized based on p24 Gag content, measured in an enzyme linked immunosorbent assay (ELISA; NEN Life Science).

Production of β-lactamase-Vpr Containing Pseudotyped HIV-1 Viral Particles

For the production of pseudotyped HIV-1 viruses, 293T cells were cotransfected with pNL4-3Δenv proviral DNA (30 μg), an envelope expressing plasmid of a virus of choice (JRFL, Ada, A-MLV, VSV-G or Ebola/Marburg envelopes) (30 μg), pCMV-BlaM-Vpr (20 μg) and pAdVAntageTM vectors (10 μg) (Invitrogen). After 48 hours of culture at 37° C., the virus-containing supernatant was centrifuged at low speed to remove cellular debris and then ultra-centrifuged at 72,000×g for 90 min at 4° C. to sediment viral particles. The virion enriched pellet was re-suspended in DMEM and aliquoted for storage at −80° C. All transfections were performed using calcium phosphate for precipitation of DNA. Viral stocks were normalized based on p24 Gag content, measured in an enzyme linked immunosorbent assay (ELISA; NEN Life Science).

Virion-Based Fusion Assay

The virion-based fusion assay was performed in three successive steps, including 1) incubation of target cells with virus particles; 2) loading of target cells with CCF2/AM dye, and 3) development and detection of the BlaM reaction. Once target cells were loaded with the CCF2 dye, the cells were maintained at room temperature to avoid export of CCF2. Since viral infections are performed at 37° C., the infection step was performed first, and then the cell cultures were subsequently loaded with the CCF2/AM dye.

For the examples below, 3×105 HeLa CD4 cells, 5×105 Jurkat of SupT1 cells, or 2×105 primary cells, were incubated with BlaM-Vpr containing virions (50 to 500 ng of p24 Gag) at 37° C. for 1–3 hours. After washing, in CO2 independent media (GibCo BRL), the cells were loaded with CCF2/AM dye according to the manufacturer's instructions (Aurora Biosciences). Briefly, 2 μl of a 1mM solution of CCF2/AM (solution A) were mixed with 8 μl of solution B containing 100 mg/mg of Puronic-F127r AND 0.1% ACE-TIC ACID. 1ml of CO2 independent media was added to constitute the loading solution. Cells were incubated in 50 μl of 100 μl of the loading solution for 1 hr at room temperature. After 2 washes with CO2 independent media, the BlaM reaction was allowed to develop for 7 hours (unless specific otherwise) at room temperature in 200 μl of DMEN supplemented with 10% fetal bovine serum (FBS) and 2.5 mM probenecid, a nonspecific inhibitor of anion (and CCF2) transport (Sigma Pharmaceuticals). No antibiotics were added to the culture media. Finally the cells were washed once in PBS and fixed in a 2% solution of paraformaldehyde.

The change in emission fluorescence of CCF2 following cleavage by the BlaM-Vpr chimera was monitored by flow cytometry using a 3 laser Vantage SE instrument (Becton Dickinson, Inc., San Jose, Calif.). A coherent krypton laser operating at 200 mW and generating light at 406.7 nm was used to excite the CCF2 dye. Blue emission was detected using an HQ455/50 filter while green emission data was collected using an HQ545/90 BP filter. Light splitting was performed using a 505 SP filter. Data were collected using CellQuest and analyzed with FlowJo software (Treestar Inc., San Carlos, Calif.). All filters were obtained from Chroma Technology, Inc (Brattleboro, Vt.). IN some examples, digital images were collected using a Nikon TE300 microscope equipped with a Hammamatsu ORCA II Dual Scan Cooled CCD Camera and an XF124 filter set from Omega Optical (Brattleboro, Vt.). Briefly, this filter set allows excitation of the fluorophore CCF2 at 400 nm (*file XF1006), and discrimination between the uncleaved CCF2 emission at 520 nm (Filter XF3002) and the cleaved CCF2 emission at 447 nm (filter XF2007). Images were captured and processed using Universal Imaging MetaMorph v4.6, and Adobe Photoshop.

Immunostaining

When heterogeneous cell populations such as human lymphoid aggregate culture (HLAC) from tonsil and spleen were examined in the virion-based fusion assay, a secondary immunostaining step was often added to allow phenotyping of the subpopulation of cells to which the β-lactamase-Vpr virions had fused. This step was performed prior to fixing of the cells in paraformaldehyde. Standard immunostaining conditions well known and practiced by those skilled in the art were employed. Briefly, the cells were washed 2 times in staining buffer (PBS-2% FBS) and then incubated for 30 min at room temperature with anti-CD3-ECD and anti-CD4-APC antibodies diluted 1/20 in staining buffer. After 2 washes, the cells were fixed and analyzed by multi-parameter flow cytometry.

Intracellular p24 Gag Staining

After 2 washes in PBS-2% FBS, the cell cultures were permeabilized by incubation at room temperature for 30 min in the ORTHO PermeaFix TM (Ortho Diagnostic System, Inc., Raritan, N.J. 08869). After 2 additional washes, the cells were incubated with monoclonal anti-p24 Gag antibody (KC67, Becton Dickinson) conjugated to FITC at a 1:20 dilution for 30 minutes at room temperature. After 2 washes the cells were fixed and analyzed by multi-parameter flow cytometry.

Example 1

Analysis of Virion Fusion in HeLa-CD4 Cells

Cultures of HeLa-CD4 cells expressing endogenous CXCR4 receptors were either mock-infected or infected for 2 hours with BlaM-Vpr-containing virions (200 ng p24-Gag) corresponding to an X4-tropic NL4-3 strain of HIV or an R5-tropic 81A strain of HIV. The CXCR4-specific inhibitor of entry, AMD3100 (250 nM) was added 1 hour prior to infection in some assays. After loading of the cells with the CCF2/AM dye, fusion was analyzed by fluorescence microscopy. The images presented correspond to an overlay of frames captured after fluorophore excitation with 495 nm and 395 nm light using the corresponding filter sets.

While no blue cells were detected in the mock-infected control culture, approximately 10% of the cells in cultures infected with HIV-1 NL4-3 displayed a deep blue color. Consistent with this color change deriving from the fusion of virions to the target cells, essentially no blue cells were detected in virally infected HeLa-CD4 cells pretreated with AMD3100, an inhibitor of CXCR4-dependent viral entry. Thus, cleavage of the CCF2 dye can be detected following infection of HeLa CD4 cells with CXCR4-tropic HIV-1 NL4-3 virions containing a β-lactamase-Vpr chimeric viral protein. Upon incubation with R5-tropic virus, endocytosis of virions was readily detected by measurement of trypsin-resistant intracellular p24-Gag levels (not shown), but no blue cells were evident in the fusion assay.

Example 2

Analysis of Virion Fusion in Human SupT1 Cells

Cultures of SupT1 cells were either mock infected or infected for 2 hours with X4-tropic NL4-3 virions containing BlaM-Vpr in the absence or in the presence of AMD3100 (250 nM) or the reverse transcriptase inhibitor, AZT (10 µM). After CCF2/AM loading, fusion was analyzed by multi-parameter flow cytometry using a violet laser for excitation of CCF2.

Figure 2:
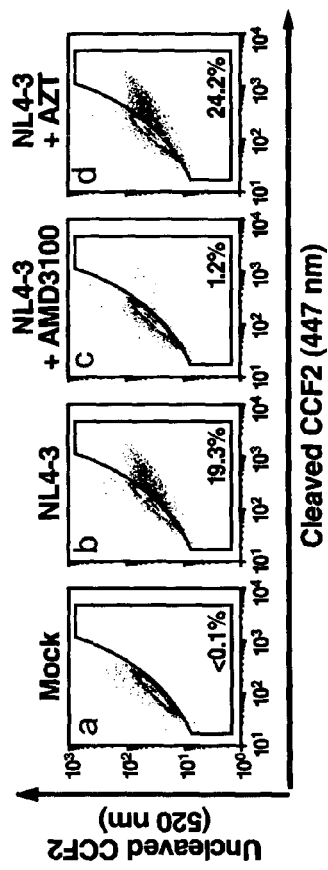
FIG. 2 is a set of scatter plots from FACS analysis and showing the results of analysis of virion fusion in human SupT1 T cells.

In the mock-infected culture (FIG. 2, panel a), the SupT1 cells were distributed on a diagonal reflecting modest differences in dye loading coupled with a low level of spontaneous degradation of the dye leading to a constant ratio of blue to green fluorescence. However, after infection with HIV-1 NL4-3 virions containing the β-lactamase-Vpr chimeric viral protein, approximately 20% of the SupT1 cells displayed a higher ratio of blue to green fluorescence, indicating active cleavage of CCF2 by β-lactamase-Vpr had occurred (FIG. 2, panel b). Such a shift to an increased blue fluorescence induced by viral infection was almost completely blocked by pretreatment of the cells with AMD3100 (FIG. 2, panel c). This blocking effect appeared specific since addition of AZT, an inhibitor of reverse transcriptase occurring later in the viral life cycle did not impair the shift to greater blue fluorescence (FIG. 2, panel d).

Together, these findings indicate that the β-lactamase-Vpr chimeric viral proteins are effectively incorporated into HIV virions, not adversely inactivated by the active HIV-1 protease, and are transmitted to both HeLa-CD4 and SupT1 cells during viral infection leading to effective cleavage of the CCF2 dye, which can be readily detected by either fluorescence microscopy or flow cytometry.

Example 3

Endocytosis of Modified Virions Does Not Lead to a Detectable Signal

Fusion-mediated entry of HIV at the plasma membrane is not the only portal for virion entry into cells. Virion endocytosis represents a very active pathway of uptake. However, in the absence of the appropriate viral receptors in the vesicles, this pathway leads to a non-productive form of infection (Marechal, V. et al. J. Virology 72:2208–2212 (1998); Schaeffer, E. et al. J. Virology 75:2993–3000 (2001)).

Figure 3:
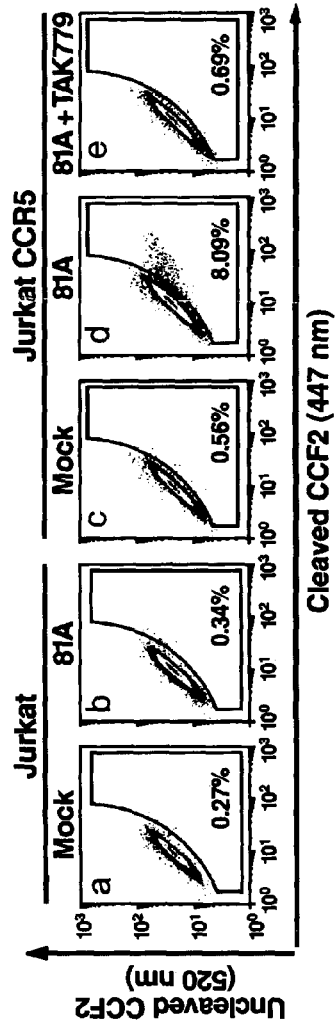
FIG. 3 is a set of scatter plots from FACS analysis and showing that endocytosis of HIV virions containing BlaM-Vpr chimeric viral protein does not lead to cleavage of the CCF2 BlaM substrate.

To investigate whether the BlaM-Vpr assay discriminates between productive and non-productive virion entry by fusion and endocytosis respectively, Jurkat T cells either expressing or not expression CCR5 were incubated with a CCR5-tropic strain of HIV-1 (81A) containing BlaM-Vpr (FIG. 3). When Jurkat T cells lacking CCR5 were infected with the R5-tropic 81A virus endocytosis of virions was readily detected by measurement of acid-resistant intracellular p24 Gag content however, no shift to increased blue fluorescence was observed (FIG. 3, panel b) relative to mock-infected control cells (FIG. 3, panel a). These 81A virions were capable of fusion as indicated by the increase in blue fluorescence obtained when these virions were incubated with Jurkat T cells expressing CCR5 (FIG. 3, panel d, compare with mock infection control in FIG. 3, panel c).

Conversely, no shift to increased blue fluorescence was observed in these CCR5-Jurkat T cells when the culture was preincubated with 250 nM TAK-779, an inhibitor of CCR5 dependent entry (Baba, M. et al. Proc. Natl. Acad. Sci. USA 96:5698–5703 (1999) (FIG. 3, panel e). Similar results were obtained with HeLa CD4 cells. Upon incubation with R5-tropic virus, endocytosis of virions was readily detected by measurement of trypsin-resistant intracellular p24 Gag levels, yet no blue cells were evident.

These results indicate that the virion-based fusion assay detects entry of virions by fusion but not by endocytosis. This specificity likely derives from the lack of substrate availability within the endosome, since the de-esterified CCF2 dye is unable to cross biological membranes and thus is trapped in the cytoplasm.

Example 4

Comparison of Viral Fusion Between Two Hours and Forty-Eight Hours

Figure 4:
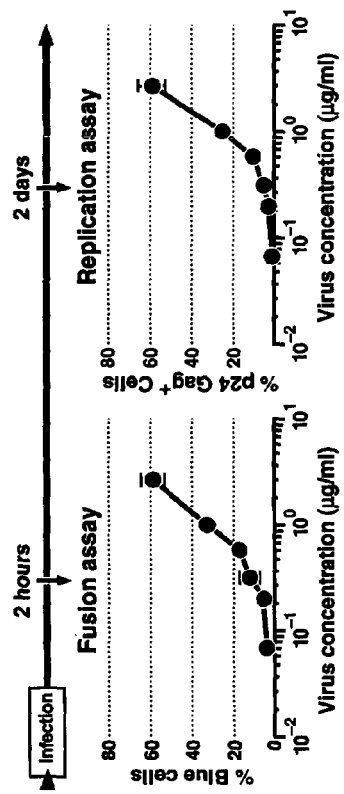
FIG. 4 is a pair of line graphs comparing HIV-1 fusion at 2 hours and HIV replication measured at 2 days in the same culture of human SupT1 cells.

Since this assay selectively detects virion entry via the productive pathway of fusion, the inventors next examined whether changes in the levels of fusion detected at 2 hours were predictive of the levels of HIV replication occurring at 48 hours as reflected by increased production of intracellular p24 Gag (FIG. 4).

$5 \times 10^5$ SupT1 cells were infected for 2 hours with serial dilutions of HIV-1 NL4-3 virions containing the BlaM-Vpr chimeric viral protein (from 0.18 to 12 µg/ml of p24-Gag). HIV-1 fusion was analyzed in the virion-based fusion assay by removal of an aliquot of cells 2 hours after infection. The remaining cells were incubated for 2 days at 37° C. to allow completion of the HIV replication cycle. To monitor productive HIV infection, the cells were subjected to intracellular staining with monoclonal anti-p24 Gag monoclonal antibodies (KC57) conjugated to fluorescein isothiocyanate (FITC). Each infection was performed in triplicate; error bars indicate standard deviations.

At 2 hours, fusion was analyzed on an aliquot of the cells (FIG. 4, left panel). The remaining cells were washed and incubated for 2 days at 37° C. to allow viral replication to occur. A close correlation between the number of cells displaying virion fusion and the number of cells staining positive for intracellular p24 Gag expression was noted. Each assay displayed dose-dependency and inter-assay comparisons revealed a clear correlation between the level of fusion and the subsequent level of viral replication in these cultures.

The correlation of the transfer of β-lactamase-Vpr (BlaM) from HIV-1 viral particles to the target cells with the number of fused virions was tested. SupT1 cells ($5 \times 10^5$) were infected for 2 h with serial dilutions of HIV-1 NL4-3 virions containing BlaM-Vpr (0.18–12 µg/ml p24-Gag). HIV-1 fusion was detected as described for the experiment that led to the results in FIG. 3, except that the BlaM reaction was allowed to develop for only 4 h. The cultures were then analyzed by flow cytometry. Mock-infected samples were used to determine the gates defining a population of "blue cells" and a population of "green cells" corresponding to the remaining non-infected cells within the samples. The geometric mean fluorescence at 447 nm of both populations was then determined. The shift in geometric mean fluorescence at 447 nm was calculated by subtracting the value of the mean fluorescence of the green population (almost a constant value) from the mean fluorescence of the "blue cells".

At the concentration of virions where the probability of dual infection is significantly increasing (i.e., when the percentage of blue cells detected is greater than 50%), a significant and progressive increase in the geometric mean of the blue fluorescence signal is observed. Thus, under conditions that progressively favored more than one fusion even per cell, the mean intensity of blue fluorescence measured at 447 nm steadily increased, indicating that the depth of color change within individual cells correlates with the number of virions fusing to these cells.

These findings underscore the quantitative features of the virion-based fusion assay and its correlation with later events in the HIV replicative life cycle.

Example 5

Application of the HIV-1 Virion Based Fusion Assay to Biologically Relevant Primary Cells.

Since a variety of cells can be loaded with the CCF2 dye, the inventors examined whether the virion-based fusion assay could be successfully applied to the study of HIV fusion in biologically relevant target cells, namely primary peripheral blood mononuclear cells (PBMCs).

Figure 5:
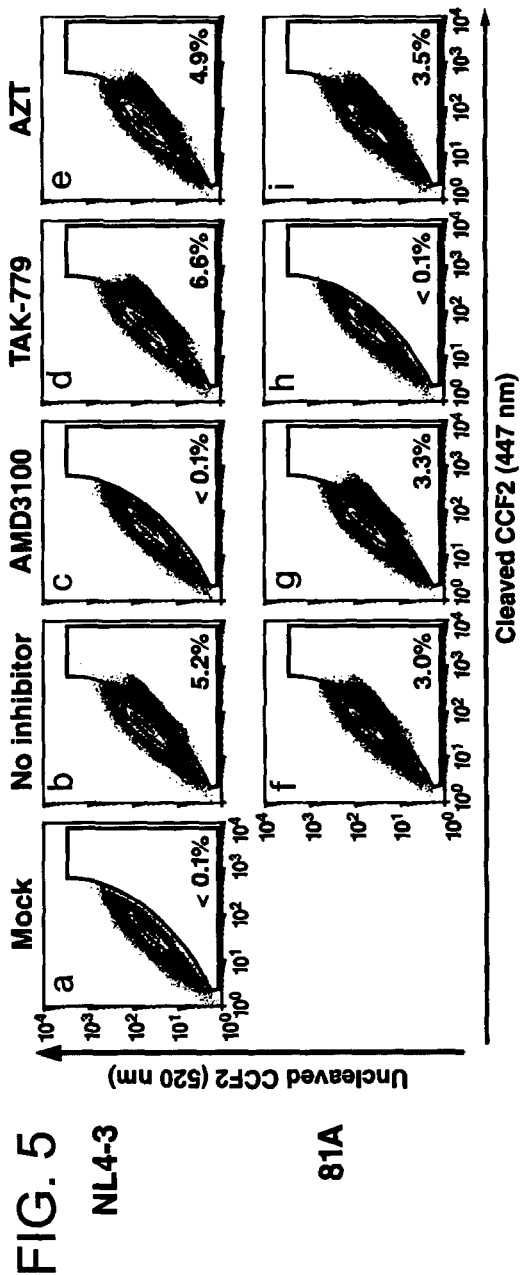
FIG. 5 is a set of scatter plots from FACS analysis of HIV fusion in cultures of primary peripheral blood mononuclear cells (PBMCs).

PBMCs were activated with phytohemagglutinin (PHA) (10 ug/ml) overnight and subsequently cultured in IL-2 (20 IU/ml) for 5 days. The cells were then either mock-infected (FIG. 5, panel a) or infected for 2 hours with 100 ng p24-Gag of X4-tropic NL4-3 virions containing the BlaM-Vpr chimeric viral protein (FIG. 5, panels b, c, d, and e) or 500 ng p24-Gag of R5-tropic 81Z virions containing the BlaM-Vpr chimeric viral protein (FIG. 5, panels f, g, h, and i) either in the absence of inhibitors (FIG. 5, panel b and f) or in the presence of AMD3100 (250 nM, FIG. 5, panel c and g), TAK-770 (250 nM, FIG. 5, panels d and h), or AZT (10 μM, FIG. 5, panels e and i). After CCF2/AM dye loading of the cells, the BlaM reaction was allowed to develop for 12 hours. Virion fusion was analyzed by multi-parameter flow cytometry.

When 2×106 PHA-stimulated PBMCs were incubated for 2 hours with CXCR4-tropic HIV-1 virions containing BlaM-Vpr chimeric viral protein (100 ng p24 Gag), 5.2% of the cells displayed evidence of fusion as indicated by a shift to greater blue fluorescence. Pretreatment of these PBMC cultures with 250 nM AMD3100 fusion inhibitor inhibited this change while, as expected, pretreatment with 10 μM AZT or with 250 nM TAK-779 produced no inhibitory effect. Addition of more virus (500 ng of p24-Gag), fusion of R5 tropic 81A virions was detected in approximately 3% of the cells.

These findings indicate that the virion-based fusion assay can be applied to study fusion in PBMC cultures.

Example 6

Analysis of HIV Fusion in Primary Cultures of Dispersed Mononuclear Cells from Human Tonsil.

Next, it was determined whether this assay may be used in conjunction with primary lymphoid cells derived from human tonsil or spleen. The Human Lymphoid Aggregate Culture (HLAC), corresponding to ex vivo cultures of dispersed spleen or tonsil tissue (Eckstein, D. A. et al, Immunity 15:671–682 (2001), represents a relevant system to study HIV infection. HLAC contains primary cells of mixed types, which are representative of primary lymphoid tissues that have become established in the absence of mitogens or cytokines and are permissive for HIV infection. Due to heterogeneous population of cells present within these cultures, it was also investigated whether it was possible to couple the HIV fusion assay with cell surface immunostaining to identify the subset of cells undergoing fusion.

As a proof of feasibility, the assay was performed using anti-CD3 and anti-CD4 antibodies, each of which was directly conjugated to a different fluorophore. Human lymphoid aggregate cultures (HLAC) prepared from human tonsil were cultured overnight and infected for 3 hours with an HIV-1 X4-tropic NL4-3 containing β-lactamase-Vpr chimeric viral protein. After CCF2/AM dye loading and incubation at room temperature to allow β-lactamase mediated degradation of the substrate, the cells were washed and immunostained with anti-CD4 and anti-CD3 antibodies conjugated to allophycocyanin (APC) and phycoerythrin-texas red (ECD), respectively. Fusion events were analyzed in the CD3+, CD4+ and CD3+, CD4− sub-population of lymphocytes.

Figure 6:
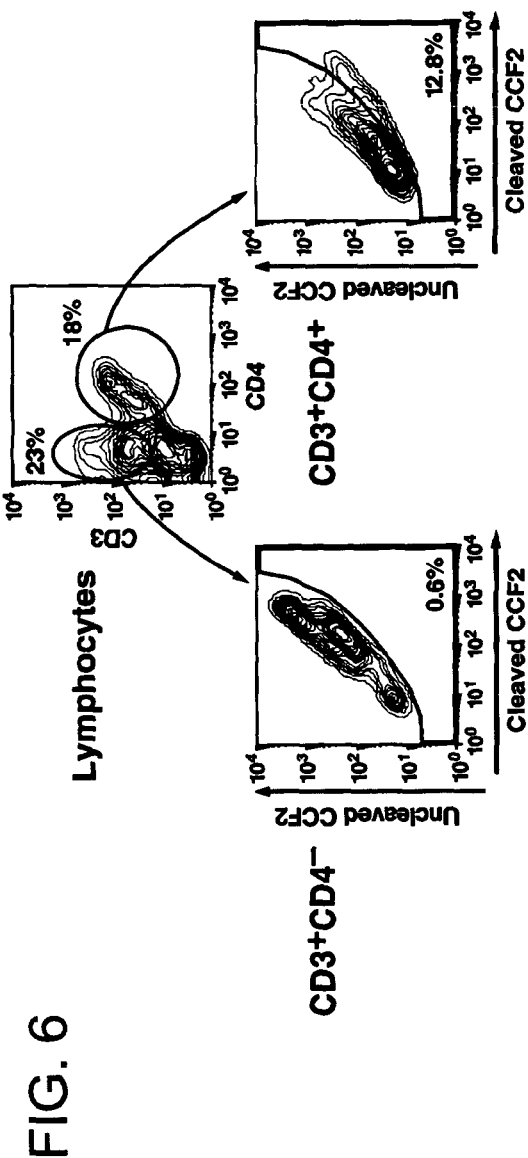
FIG. 6 is a set of scatter plots from FACS analysis of HIV fusion in primary cultures of dispersed mononuclear cells from human tonsil.
Figure 7:
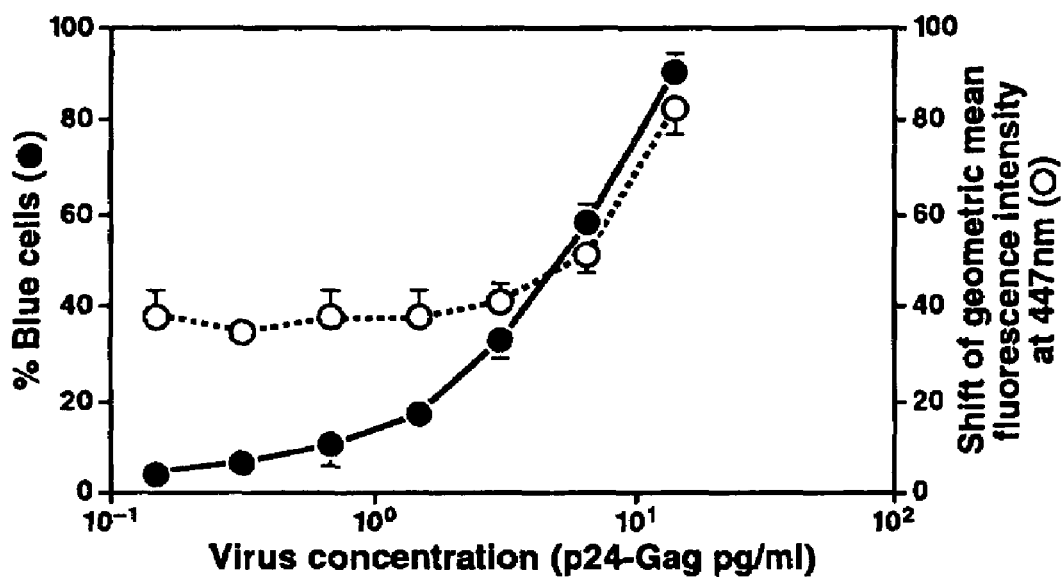
FIG. 7 is a graph illustrating the shift in the blue fluorescence with increasing viral concentration. Each infection was performed in triplicate; error bars indicate standard deviations.

The fusion assay was performed as with the PBMCs except that an immunostaining step with anti-CD3 and anti-CD4 antibodies was performed prior to treatment with paraformaldehyde (PFA) (FIG. 6). The CD3 and CD4 antibodies defined three populations within the lymphocyte gate identified by forward and side scattering. The CD3−,CD4− population was principally composed of B cells, while the CD3+, CD4+ population represented CD4 T cells and the CD3+, CD4− cells were principally composed of CD8+ T lymphocytes. When these populations were examined for evidence of HIV-1 virion fusion, 13% of the CD3+, CD4+ cells displayed a shift to increased blue fluorescence while almost none of the CD8+ T lymphocytes (CD3+, CD4−) displayed such changes.

These results demonstrate that this virion based assay can be applied to study fusion in complex cultures of primary lymphocytes derived from lymphatic tissues. Furthermore, the results suggest that the fusion assay can be coupled with immunostaining to order to identify and characterize the subset of cells that undergo fusion with a viral particle.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for detecting fusion of an enveloped retrovirus to a target cell, the method comprising:

contacting a target cell with an enveloped retroviral virion, the virion containing a chimeric viral protein comprising a reporter polypeptide operably joined to a viral accessory protein, wherein the reporter polypeptide provides a detectable signal by cleaving a substrate in the target cell upon intracellular delivery of the chimeric viral protein into the target cell cytoplasm, wherein the substrate is retained in the cytoplasm and is not present at a significantly detectable level in an endosome; and wherein the detectable signal is not detectable prior to said intracellular delivery into the target cell cytoplasm; and detecting the presence or absence of the detectable signal;
wherein the presence of the detectable signal indicates the virion has entered the target cell by viral fusion and not by endocytosis.

2. The method of claim 1, wherein the enveloped retroviral virion is a human immunodeficiency virus (HIV) virion.

3. The method of claim 2, wherein the chimeric viral protein comprises beta-lactamase (BlaM) operably linked to Viral protein R (Vpr).

4. The method of claim 1, wherein the reporter polypeptide is beta-lactamase.

5. The method of claim 4, wherein the substrate is coumarin cephalosporin fluorescein (CCF2).

6. The method of claim 1, wherein the viral accessory protein of the chimeric viral protein is Viral protein R (Vpr).

7. The method of claim 1, wherein the reporter polypeptide is beta-lactamase (BlaM).

8. The method of claim 1, wherein the chimeric viral protein comprises beta-lactatmase (BlaM) operably joined to Viral protein R (Vpr).

9. The method of claim 8, wherein BlaM and Vpr are joined through a spacer peptide.

10. The method of claim 1, wherein the retroviral virion is a pseudotyped virion, and wherein the envelope protein of the pseudotyped virion is not endogenous to the retroviral virion.

11. A method for detecting fusion of an human inmmunodeficiency virus (HIV) virion to a target cell, the method comprising:
contacting a target cell with an HIV virion containing a chimeric viral protein, wherein the chimeric viral protein comprises a beta-lactamase (BlaM) polypeptide operably linked to a viral accessory protein, and wherein the cell contains a BlaM substrate which is retained in the cytoplasm and is not present at a significantly detectable level in an endosome, wherein intracellular introduction of the chimeric viral protein into the target cell cytoplasm results in cleavage of the substrate by BlaM and production of a detectable signal;
wherein detection of the detectable signal indicates that the HIV virion has entered the target cell by viral fusion and not by endocytosis.

12. The method of claim 11, wherein the viral accessory protein of the chimeric viral protein is Viral protein R (Vpr).

13. The method of claim 12, wherein BlaM and Vpr are operably linked through a spacer peptide.

14. The method of claim 11, wherein the HIV virion is a pseudotyped HIV virion, and wherein the envelope protein of the pseudotyped virion is not endogenous to the HIV virion.

* * * * *

UNITED STATES PATENT AND TRADEMARK OFFICE
CERTIFICATE OF CORRECTION

| | | |
|---|---|---|
| PATENT NO. | : 7,250,251 B2 | Page 1 of 1 |
| APPLICATION NO. | : 10/656803 | |
| DATED | : July 31, 2007 | |
| INVENTOR(S) | : Warner C. Greene | |

It is certified that error appears in the above-identified patent and that said Letters Patent is hereby corrected as shown below:

Please replace the statement regarding Government Rights beginning on column 1, line 10, with the following revised statement:

GOVERNMENT RIGHTS

This invention was made with government support under federal grant no. NIH P01 HD40543 awarded by the National Institutes of Health. The United States Government has certain rights in this invention.

Signed and Sealed this

Sixteenth Day of March, 2010

David J. Kappos
*Director of the United States Patent and Trademark Office*